(12) United States Patent
Graves et al.

(10) Patent No.: US 8,727,216 B2
(45) Date of Patent: May 20, 2014

(54) PORTABLE MEMORY MODULE WITH WIRELESS EMITTER TO FACILITATE THE PROVISION OF LOCATION-DEPENDENT SERVICES

(75) Inventors: Alan Graves, Kanata (CA); Jeffrey Fitchett, Kanata (CA); Brian Vezza, Allen, TX (US)

(73) Assignee: Apple Inc., Cupertino, CA (US)

( * ) Notice: Subject to any disclaimer, the term of this patent is extended or adjusted under 35 U.S.C. 154(b) by 1743 days.

(21) Appl. No.: 12/155,899

(22) Filed: Jun. 11, 2008

(65) Prior Publication Data

US 2009/0140043 A1    Jun. 4, 2009

Related U.S. Application Data

(60) Provisional application No. 60/991,839, filed on Dec. 3, 2007.

(51) Int. Cl.
*G06K 7/00* (2006.01)
*G06K 19/06* (2006.01)
*G06F 15/00* (2006.01)
*G01S 1/00* (2006.01)
*G01S 3/02* (2006.01)

(52) U.S. Cl.
USPC ........... 235/439; 235/375; 235/492; 342/385; 342/450

(58) Field of Classification Search
USPC .......... 235/491, 375, 435, 439, 492; 705/2–3; 340/572.1; 342/385, 450
See application file for complete search history.

(56) References Cited

U.S. PATENT DOCUMENTS 4,601,064 A    7/1986  Shipley
5,291,399 A    3/1994  Chaco
(Continued)

FOREIGN PATENT DOCUMENTS

BG    0602906.0    6/2006
CA    2263428    2/1998
(Continued)

OTHER PUBLICATIONS

Swedberg, Ford Deploys RFID-Enabled Chargers, RFID Journal, http://www.rfidjournal.com/article/view/1348/1/1/, Jan. 19, 2005, 3 p.

(Continued)

*Primary Examiner* — Michael G Lee
*Assistant Examiner* — Laura Gudorf
(74) *Attorney, Agent, or Firm* — Fay Kaplun & Marcin, LLP (57) ABSTRACT

A portable memory module, which comprises an interface allowing the module to be connected to and disconnected from an electronic device by a user of the module such that the electronic device is in close physical proximity to the module when connected thereto; memory storing an identifier of the module; an emitter; and a processing entity configured to encode the identifier of the module into a signal that is transmitted via the emitter as a wireless beacon. The memory contains information that allows the module to be identified by an entity connected to the electronic device. The wireless beacon is configured to enable a location of the module to be determined by a detection sub-system. When the module is connected to the electronic device and the identity of the module is transmitted to a network entity via the electronic device, the location of the module can be used by the network entity to establish the location of the electronic device.

28 Claims, 7 Drawing Sheets

(56) References Cited

U.S. PATENT DOCUMENTS

| | | |
|---|---|---|
| 5,434,775 A | 7/1995 | Sims et al. |
| 5,465,082 A | 11/1995 | Chaco |
| 5,534,851 A | 7/1996 | Russek |
| 5,544,661 A | 8/1996 | Davis et al. |
| 5,594,786 A | 1/1997 | Chaco et al. |
| 5,610,596 A | 3/1997 | Petitclerc |
| 5,689,229 A | 11/1997 | Chaco et al. |
| 5,822,544 A | 10/1998 | Chaco et al. |
| 5,877,675 A | 3/1999 | Rebstock et al. |
| 5,901,172 A | 5/1999 | Fontana et al. |
| 5,910,776 A | 6/1999 | Black |
| 5,911,687 A | 6/1999 | Sato et al. |
| 5,942,986 A | 8/1999 | Shabot et al. |
| 6,009,333 A | 12/1999 | Chaco |
| 6,026,125 A | 2/2000 | Larrick, Jr. et al. |
| 6,054,950 A | 4/2000 | Fontana |
| 6,211,790 B1 | 4/2001 | Radomsky et al. |
| 6,239,741 B1 | 5/2001 | Fontana et al. |
| 6,259,355 B1 | 7/2001 | Chaco et al. |
| 6,262,662 B1 | 7/2001 | Back et al. |
| RE37,531 E | 1/2002 | Chaco et al. |
| 6,344,794 B1 | 2/2002 | Ulrich et al. |
| 6,462,656 B2 | 10/2002 | Ulrich et al. |
| 6,539,393 B1 | 3/2003 | Kabala |
| 6,577,238 B1 | 6/2003 | Whitesmith et al. |
| 6,662,068 B1 | 12/2003 | Ghaffari |
| 6,690,741 B1 | 2/2004 | Larrick, Jr. et al. |
| 6,753,671 B1 | 6/2004 | Harvey |
| 6,773,396 B2 | 8/2004 | Flach et al. |
| 6,812,884 B2 | 11/2004 | Richley et al. |
| 6,823,199 B2 | 11/2004 | Gough |
| 6,825,763 B2 | 11/2004 | Ulrich et al. |
| 6,870,916 B2 | 3/2005 | Henrikson et al. |
| 6,876,303 B2 | 4/2005 | Reeder et al. |
| 6,958,677 B1 | 10/2005 | Carter |
| 6,958,706 B2 | 10/2005 | Chaco et al. |
| 6,972,683 B2 | 12/2005 | Lestienne et al. |
| 7,042,337 B2 | 5/2006 | Borders et al. |
| 7,080,061 B2 | 7/2006 | Kabala |
| 7,154,397 B2 | 12/2006 | Zerhusen et al. |
| 7,242,306 B2 | 7/2007 | Wildman et al. |
| 7,283,037 B2 | 10/2007 | Diorio et al. |
| 2001/0044731 A1 | 11/2001 | Coffman et al. |
| 2002/0044043 A1 | 4/2002 | Chaco et al. |
| 2002/0044059 A1 | 4/2002 | Reeder et al. |
| 2002/0147912 A1 | 10/2002 | Schmueli et al. |
| 2002/0183078 A1 | 12/2002 | Hase |
| 2002/0183979 A1 | 12/2002 | Wildman |
| 2003/0078810 A1 | 4/2003 | Cole et al. |
| 2003/0078811 A1 | 4/2003 | Cole et al. |
| 2003/0132845 A1 | 7/2003 | McDaniels, III |
| 2004/0001446 A1 | 1/2004 | Bhatia et al. |
| 2004/0004460 A1 | 1/2004 | Fitch et al. |
| 2004/0008114 A1 | 1/2004 | Sawyer |
| 2004/0034284 A1 | 2/2004 | Aversano et al. |
| 2004/0078219 A1 | 4/2004 | Kaylor et al. |
| 2004/0100376 A1 | 5/2004 | Lye et al. |
| 2004/0108954 A1 | 6/2004 | Richley et al. |
| 2004/0153344 A1 | 8/2004 | Bui et al. |
| 2004/0178947 A1 | 9/2004 | Richley et al. |
| 2004/0186357 A1 | 9/2004 | Soderberg et al. |
| 2004/0193449 A1 | 9/2004 | Wildman et al. |
| 2004/0252015 A1 | 12/2004 | Galperin et al. |
| 2004/0257224 A1 | 12/2004 | Sajkowsky |
| 2005/0017864 A1 | 1/2005 | Tsoukalis |
| 2005/0027465 A1 | 2/2005 | Pozgay et al. |
| 2005/0035862 A1 | 2/2005 | Wildman et al. |
| 2005/0148831 A1 | 7/2005 | Shibata et al. |
| 2005/0151641 A1 | 7/2005 | Ulrich et al. |
| 2005/0153681 A1 | 7/2005 | Hanson |
| 2005/0168341 A1 | 8/2005 | Reeder et al. |
| 2005/0188095 A1 | 8/2005 | Gardiner et al. |
| 2005/0201345 A1 | 9/2005 | Williamson |
| 2005/0283382 A1 | 12/2005 | Donoghue et al. |
| 2006/0006999 A1 | 1/2006 | Walczyk et al. |
| 2006/0143043 A1 | 6/2006 | McCallie, Jr. et al. |
| 2006/0240771 A1* | 10/2006 | Graves et al. .................. 455/39 |
| 2006/0282459 A1 | 12/2006 | Kabala |
| 2007/0135866 A1* | 6/2007 | Baker et al. ..................... 607/60 |
| 2007/0296581 A1* | 12/2007 | Schnee et al. ............. 340/572.1 |

FOREIGN PATENT DOCUMENTS

| | | |
|---|---|---|
| CA | 2362635 | 8/2000 |
| CA | 2373241 | 11/2000 |
| CA | 2434714 | 8/2002 |
| EP | 0 369 662 | 5/1990 |
| EP | 0973316 | 1/2000 |
| EP | 1 101 437 | 5/2001 |
| EP | 1156336 | 11/2001 |
| EP | 1536306 | 6/2005 |
| GB | 2320397 | 6/1998 |
| GB | 2355889 | 5/2001 |
| GB | 0602885.6 | 6/2006 |
| GB | 0602887.2 | 6/2006 |
| GB | 0602901.1 | 6/2006 |
| GB | 0602903.7 | 6/2006 |
| GB | 0602904.5 | 6/2006 |
| GB | 0602907.8 | 6/2006 |
| JP | 2002/157040 | 5/2002 |
| JP | 2003/189359 | 7/2003 |
| WO | WO 95/01617 | 1/1995 |
| WO | WO 99/04685 | 2/1999 |
| WO | WO 9964974 | 12/1999 |
| WO | WO 00/52498 | 9/2000 |
| WO | WO 2004/032019 | 4/2004 |
| WO | WO 2004/042563 | 5/2004 |
| WO | WO 2004/102457 | 11/2004 |
| WO | WO 2005/043402 | 5/2005 |
| WO | PCT/CA2006/000195 | 5/2006 |
| WO | PCT/CA2006/000196 | 5/2006 |
| WO | PCT/CA2006/000197 | 5/2006 |
| WO | PCT/CA2006/000205 | 5/2006 |
| WO | WO 2006/049728 | 5/2006 |
| WO | PCT/CA2006/000198 | 6/2006 |
| WO | PCT/CA2006/000203 | 6/2006 |
| WO | PCT/CA2006/000204 | 6/2006 |
| WO | PCT/CA2006/001479 | 12/2006 |

OTHER PUBLICATIONS

Collins, RFID Remedy for Medical Errors, RFID Journal, http://www.rfidjournal.com/article/view/961, May 28, 2004, 3 p.

Weissman, "Indoor Location", downloaded from website of Tadlys Ltd., www.tadlys.com (Rishon LeZiyyon, Israel), Jul. 2004, 15 p.

Graves et al., "Applications and Solutions for Healthcare-Hospitals. A Perspective on ECAS", Version 1,0, Nortel Advanced Technology Research, Dec. 20, 2006, 226 p.

Project MESA: An Update, MESA organization, Sep. 2003, 7 p.

Chronaki et al., "WebOnCOLL: Medical Collaboration in Regional Healthcare Netwoks", IEEE Transactions on Information Technology in Biomedicine vol. 1, No. 4, Dec. 1997, p. 257-269.

Rodriguez et al., "Location-Aware Access to Hospital Information and Services", IEEE Transactions on Information Technology in Biomedicine, vol. 8, No. 4, Dec. 2004 p. 448-454.

Parco Merged Media Corporation, "The Parco Real Time Location System", Downloaded from website of Parco Merged Media Corporation: www.parcowireless.com (Portland, Maine, U.S.A.), Feb. 2005, 5 p.

Parco Merged Media Corporation, "Improving the Availability of Information", downloaded from website of Parco Merged Media Corporation, www.parcowireless.com (Portland, Maine, U.S.A.), Jan. 2005, 8 p.

Parco Merged Media Corporation, "The PARCO Wireless Health Care System (WHCS)", downloaded from website of Parco Merged Media Corporation, www.parcowireless.com (Portland, Maine, U.S.A.), Aug. 2004, 8 p.

Office Action Mailed on May 16, 2008 in connection with U.S. Appl. No. 11/065,396.

Fontana, "Experimental Results From an Ultra Wideband Precision Geolocation System", Downloaded from website of Multispectral Solutions, Inc., www.multispectral.com (Germantown, Maryland, U.S.A.), Aug. 2004, 9 p.

(56) References Cited

OTHER PUBLICATIONS

Fontana et al., "Ultra-Wideband Asset Location System", Downloaded from website of Multispectral Solutions, Inc., www.multispectral.com (Germantown, Maryland, U.S.A.), Aug. 2004, 5 p.

Fontana et al., "Commercialization of an Ultra Wideband Precision Asset Location System", Downloaded from website of Multispectral Solutions, Inc., www.multispectral.com (Germantown, Maryland, U.S.A.), Aug. 2004, 5 p.

* cited by examiner

PORTABLE MEMORY MODULE WITH WIRELESS EMITTER TO FACILITATE THE PROVISION OF LOCATION-DEPENDENT SERVICES

CROSS-REFERENCE TO RELATED APPLICATION

The present application claims the benefit under 35 U.S.C. §119(e) of U.S. Provisional Patent Application Ser. No. 60/991,839 to Graves et al., filed Jan. 2, 2008, hereby incorporated by reference herein.

BACKGROUND

It is known to configure an electronic device with personalized settings stored on a memory module such as a USB key. This ability to "personalize" the electronic device can be useful in a number of contexts such as in a healthcare environment, where different clinicians of widely varying skill sets and backgrounds share a network of generic terminals. A given clinician can even be provided with access to intelligent, location-dependent services if the terminals are fixed and the network knows each terminal's fixed location.

However, the ability of current systems to offer location-dependent services is severely impaired when the location of the point from which a user is accessing the network is unknown. This situation is not uncommon and may arise, for example, when a clinician accesses a mobile or movable electronic device capable of being transported within a hospital. It would therefore be desirable to extend the provision of location-dependent services to users of mobile or movable networked electronic devices of various kinds, particularly in a healthcare environment.

It is further known that the application of smart context aware solutions can enable major new capabilities in a healthcare environment, but to do so requires that all of the relevant personnel and equipment be equipped with location tracking devices and be personalized into the so-called environment- and context-aware system (ECAS). This can be a large undertaking for an early-phase deployment when a few clinicians will be using the system so an approach is needed whereby not all equipment (or clinicians) are outfitted with location tracking devices before the first clinicians can use the system.

SUMMARY

According to a first aspect, the present invention seeks to provide a portable memory module, comprising: an interface allowing the module to be connected to and disconnected from an electronic device by a user of the module such that the electronic device is in close physical proximity to the module when connected thereto; memory storing an identifier of the module; an emitter; and a processing entity configured to encode the identifier of the module into a signal that is transmitted via the emitter as a wireless beacon. The memory contains information that allows the module to be identified by an entity connected to the electronic device. The wireless beacon is configured to enable a location of the module to be determined by a detection sub-system.

According to a second aspect, the present invention seeks to provide a system, comprising: a portable module having an emitter for emitting a wireless beacon that allows a location of the module to be determined by a detection sub-system, the module comprising an interface; and an electronic device having an interface complementary to the interface of the module such that the electronic device is in close physical proximity to the module when said interfaces are connected, wherein the electronic device is configured to determine an identifier of the module and to inform a network entity of the identifier of the module, thereby allowing the network entity to establish that the electronic device is in close physical proximity to the module when said interfaces are connected.

According to a third aspect, the present invention seeks to provide a method, comprising: communicating with an electronic device to determine that a connection-based association indicative of close physical proximity has been formed between a portable module and the electronic device; determining a location of the module based on receipt of a wireless beacon emitted by the module; correlating the location of the module with the association between the portable module and the electronic device to establish that the electronic device has a location in close physical proximity to the location of the module; and causing the location of the module to be recorded in memory in association with the electronic device.

According to a fourth aspect, the present invention seeks to provide a computer-readable storage medium comprising a set of instructions for execution by a computing device, wherein execution of the set of instructions by the computing device causes the computing device to execute a method that includes: communicating with an electronic device to determine that a connection-based association indicative of close physical proximity has been formed between a portable module and the electronic device; determining a location of the module based on receipt of a wireless beacon emitted by the module; correlating the location of the module with the association between the portable module and the electronic device to establish that the electronic device has a location in close, physical proximity to the location of the module; and causing the location of the module to be recorded in memory in association with the electronic device.

According to a fifth aspect, the present invention seeks to provide a system, comprising: a communications network for communicating with a set of electronic devices; a detection sub-system for determining respective locations of a set of portable modules based on receipt of wireless beacons emitted by the modules; and a network processing entity configured to determine when a contact-based association indicative of close physical proximity has been formed between a particular module and a particular electronic device and to correlate the location of the particular module with the association between the particular module and the particular electronic device to establish that the particular electronic device has a location that is in close physical proximity to the location of the particular module.

DETAILED DESCRIPTION

Figure 1A:
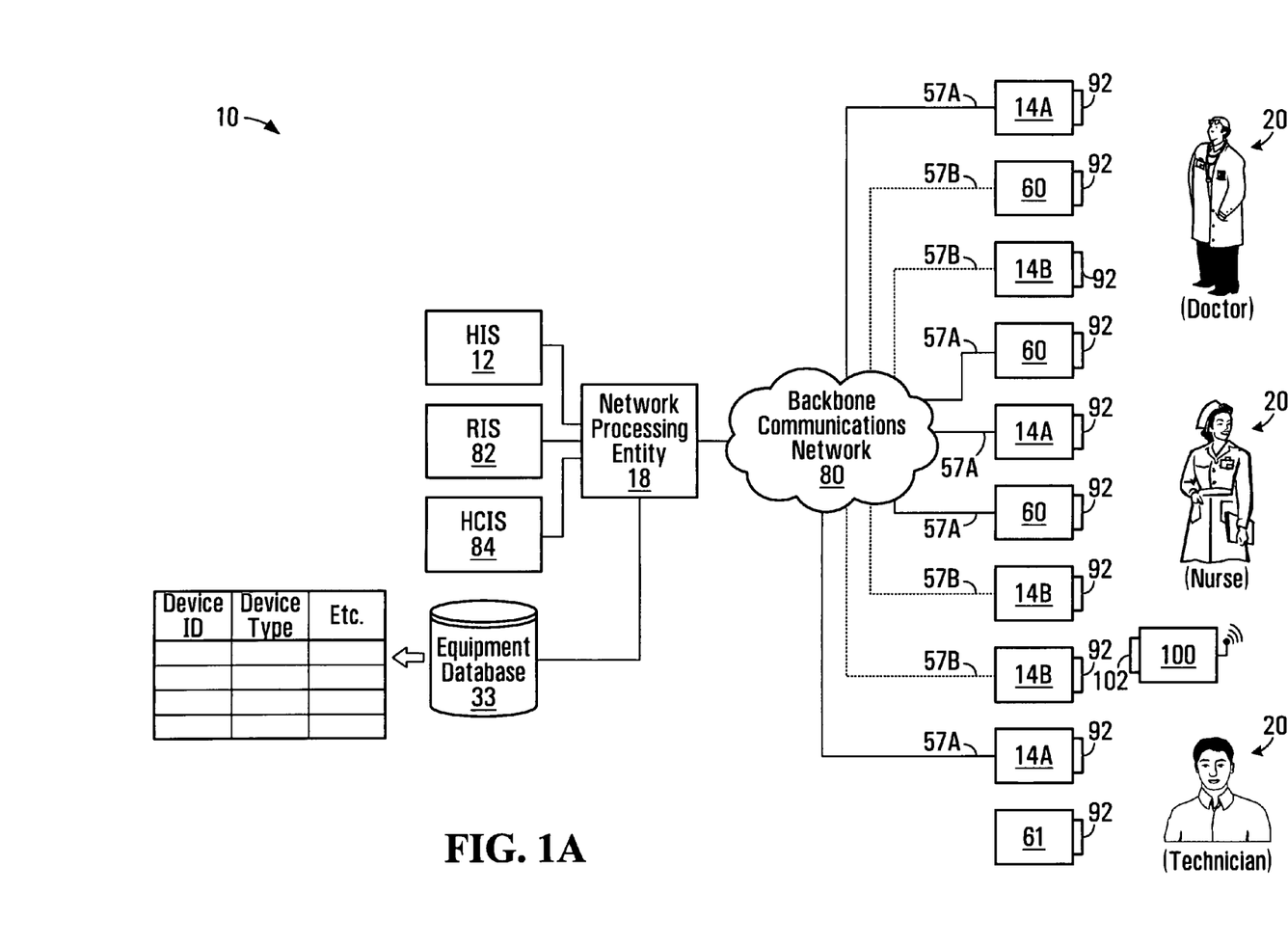
FIG. 1A is a conceptual block diagrammatic view of a communications architecture in accordance with a non-limiting example embodiment of the present invention, in which the architecture includes a plurality of electronic devices and a portable memory module.

FIG. 1A shows a conceptual view of a communications architecture 10 in accordance with an example of implementation of the present invention. In a specific non-limiting example, the communications architecture 10 can be implemented in a healthcare establishment. The healthcare establishment, such as a hospital, may physically consist of a single building or it may encompass a campus including one or more buildings or pavilions and possibly one or more adjacent areas such as roads and parking lots.

The communications architecture 10 provides a plurality of terminals 14A, 14B that are connected to a backbone communications network 80. The terminals 14A, 14B are accessed by a plurality of clinicians 20 who are mobile within the healthcare establishment. The term "clinician" is used to denote any individual who may require access to the communications network 10 in the execution of their duties pertaining to diagnosis and/or treatment of one or more patients. Clinicians 20 can include physicians, radiologists, pharmacists, interns, nurses, laboratory technicians and orderlies. This is not an exclusive list, however, and when interpreting the present invention, the word "clinician" should not be construed as limiting the invention to applicability in an environment where individuals are required to have specific medical qualifications.

The backbone communications network 80 carries information from the terminals 14A, 14B to a network processing entity 18 and vice versa. In the present non-limiting example embodiment, terminals 14A are wired terminals, such as stationary or movable terminals or workstations, while terminals 14B are wireless terminals, such as handheld units, networked personal digital assistants, smart phones, laptop computers, tablet computers, etc. Wired terminals 14A are connected to the network processing entity 18 via communication links 57A that can include primarily wired portions, whereas wireless terminals 14B communicate with the network processing entity 18 via communication links 57B that include wireless portions. The wireless portions of the communication links 57B are secure links that may be encapsulated within the backbone communications network 80, or may involve an external network connection, as would be the case when wireless terminals 14B are cellular phones or cellular data devices.

The communications architecture 10 also provides various medical devices 60 that are connected to the backbone communications network 80. Non-limiting examples of medical devices 60 include equipment that is used to input data to, or extract data from, a hospital information system (HIS) 12, a radiology information system (RIS) 82 and/or a hospital clinical information system (HCIS) 84. Non-limiting examples of medical devices 60 include CAT scanners and MRI scanners as well as smaller and more numerous devices such as patient monitors, EEG's and EKG's, controllable or monitored infusion pumps, clinician hand-held terminals, etc. Some of the medical devices 60 may be stationary or movable in character and thus may be connected to the backbone communications network 80 via communication links 57A, while other ones of the medical devices 60 may be mobile in character and thus may be connected to the backbone communications network 80 via communication links 57B. The communications architecture 10 also provides medical or other devices 61 having no network connection.

Each of the wired terminals 14A, wireless terminals 14B and medical devices 60 can be referred to generally as an "electronic device" and is associated with a unique device ID. The device ID can be a MAC address, serial number, etc. An equipment database 35 stores the device ID for each of the electronic devices 14A, 14B, 60 in association with other data such as a device type (e.g., wired terminal, wireless terminal, medical device), a device sub-type (e.g., PDA, fetal heart monitor, etc.) and/or a device display capability, to name a few non-limiting possibilities. The equipment database 35 is accessible to the network processing entity 18.

In one embodiment, some or all of the wired terminals 14A, 14B and medical devices 60 are equipped with a keyboard, keypad or other input device. In addition or alternatively, some or all of the wired terminals 14A, 14B and medical devices 60 comprise an interface 92 for receiving a portable memory module 100. In a non-limiting example, the interface 92 can be a Universal Serial Bus (USB) port.

Figure 2:
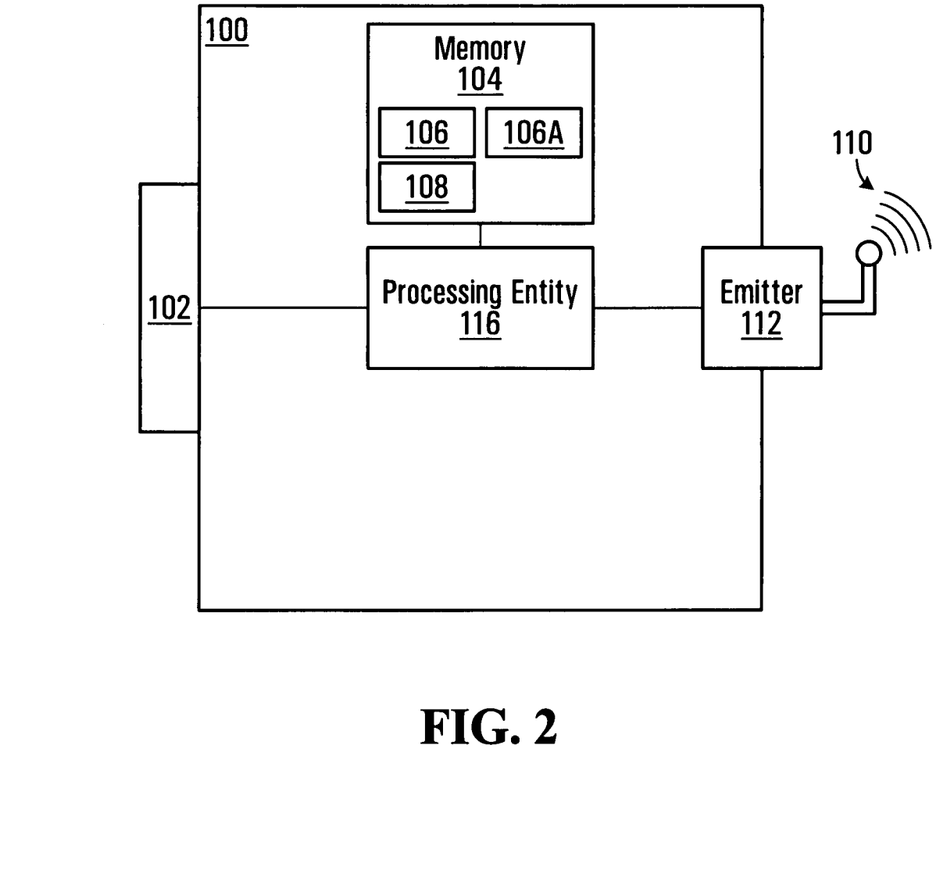
FIG. 2 shows the portable memory module of FIG. 1A in greater detail, in accordance with a non-limiting embodiment of the present invention.

In accordance with an embodiment of the present invention, and with reference to FIG. 2, the module 100 includes an interface 102 that is complementary to the interface 92. This allows a user to connect the module 100 to, and disconnect the module 100 from, an external electronic device.

The module 100 also includes memory 104, which stores an identifier 106 that uniquely identifies the module 100. The identifier 106 is hereinafter referred to as a "tag ID". In a non-limiting example, the tag ID 106 can contain a serial number or MAC-address of the module 100. The memory 104 may also store a secondary tag ID 106A which is pre-associated with the tag ID 106 and may be shorter or may include a mnemonic. The memory 104 may also store configuration information 108, allowing configuration of the electronic device to which the module 100 is ultimately connected. This is particularly useful when the module 100 is assigned to a user such as a particular clinician. Non-limiting examples of the configuration information 108 can include an identity of the particular clinician and/or the particular clinician's system preferences, application preferences or terminal configuration preferences.

The module 100 also includes a processing entity 116 with circuitry, control logic and/or software that is suitably configured to provide the external electronic device with the tag ID 106 (or the secondary tag ID 106A) via the interface 102. The processing entity 116 is also configured to encode the tag ID 106 into a signal that is transmitted via an emitter 112 in the form of a wireless beacon 110. In a non-limiting embodiment, the wireless beacon 110 can be a brief radio frequency signal. In some non-limiting embodiments, the emitter 112 can be active (i.e., it emits the wireless beacon in an autonomous fashion), while in other non-limiting embodiments, the emitter 112 can be semi-active (i.e., it emits the wireless beacon a signal only in response to being interrogated), and in still other non-limiting embodiments, the emitter 112 can be passive (i.e., it reflects a received signal).

The emitter type (e.g., active, semi-active, passive, etc.) will depend on various desiderata such as range, precision, power consumption, battery lifetime, weight and possibly other considerations. Also, care should be taken to ensure that the wireless beacon 110 emitted by the emitter 112 does not interfere with sensitive medical equipment, which may include certain ones of the medical devices 60. In some cases, the use of a low-power multi-GHz Ultra Wideband (UWB) solution, which operates with nanosecond RF bursts at a peak instantaneous power of 15-30 mW or even less (giving an average power in the nanowatt or picowatt range), may provide satisfactory performance for an active emitter. Various other solutions exist for active, passive and semi-active emitters, including solutions based on technologies other than RF propagation, including acoustic and ultrasound pings and round trip delay measurements.

Figure 1B:
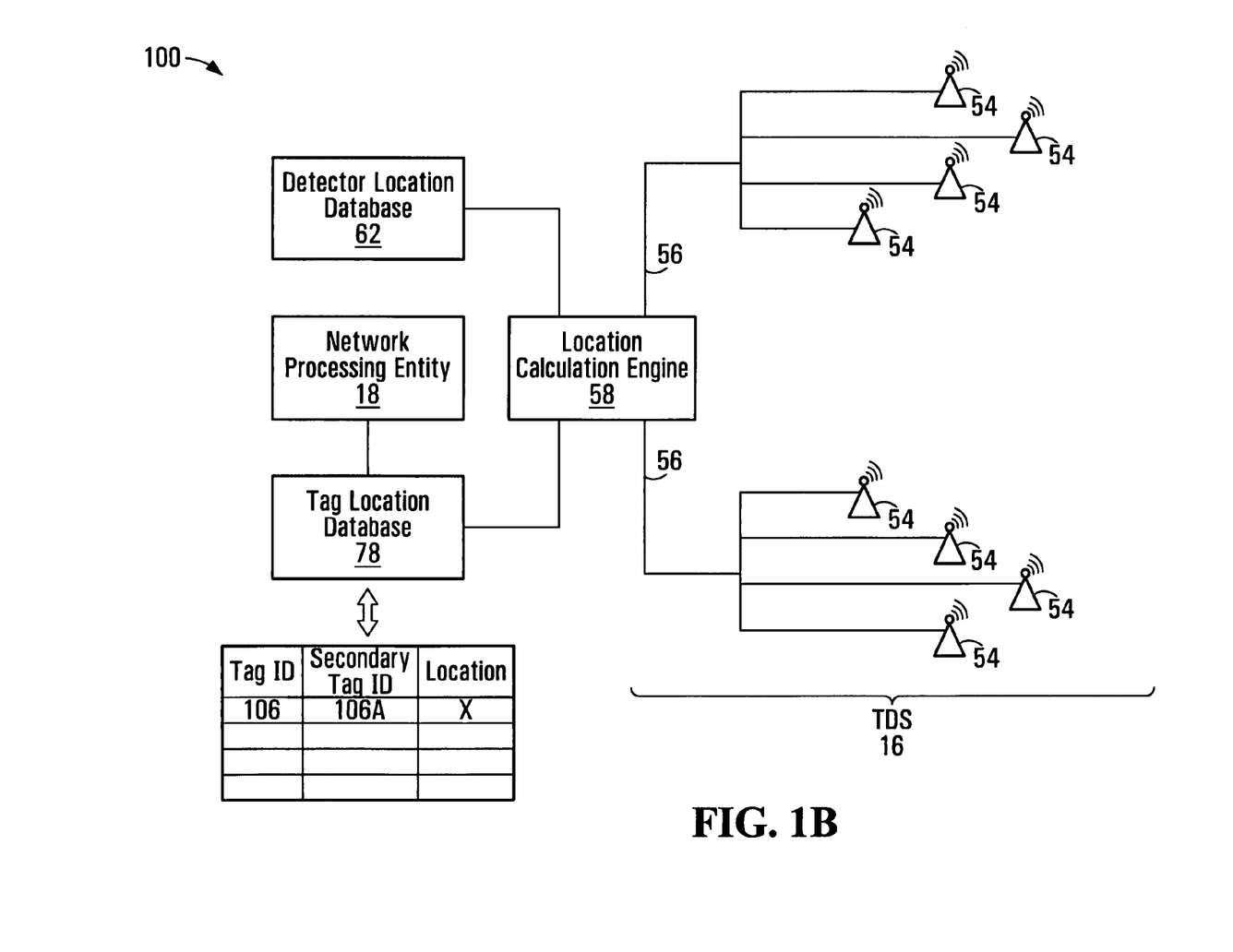
FIG. 1B shows a detection sub-system used in the communications architecture of FIG. 1A to locate beacon-emitting devices, such as the portable memory module.

With reference to FIG. 1B, the wireless beacon 110 emitted by the emitter 112 is received by a tag detection sub-system (TDS) 16 provided in the communications architecture 10. The TDS 16 determines and tracks the location of the module 100 as well as other similar portable memory modules (not shown). To this end, the TDS 16 includes a plurality of contact-less tag detectors 54 and a location calculation engine 58, which may be integrated with the network processing entity 18 or separate therefrom. The location calculation engine 58 is connected to the tag detectors 54 by a set of communication links 56.

The detectors 54 can be distributed throughout the healthcare establishment. They are positioned at known locations and may take the form of a grid or an array. Specifically, the locations of the detectors 54 may be kept in a detector location database 62 accessible to the location calculation engine 58. In addition, the detectors 54 may span multiple floors of a common building, thus effectively being distributed in three dimensions. Also, several detectors 54 may occupy different vertical positions on a given floor, thereby offering an improved capability for z-axis spatial resolution within that floor.

Typically, the detectors 54 are at known fixed locations, but they may also be at movable locations, where the location is continually calculated (by any suitable), with the detector location database 62 being updated periodically. The detectors 54 can also be build into a subset of terminals 14 and devices 60 or 61.

Depending on the emitter type (e.g., active, semi-active, passive, etc.), individual ones of the detectors 54 may include either simply a receiver for receiving the wireless beacon 110 (in the case of an active emitter), or both a transmitter for sending radio frequency pulses and a receiver for receiving the wireless beacon 110 (in the case of a semi-active or passive emitter).

Each of the detectors 54 detects the presence of emitters (and hence portable memory modules equipped with those emitters, such as the module 100 equipped with the emitter 112) in a surrounding three-dimensional volume which is a coverage zone for that detector. The union of the coverage zones for all of the detectors 54 defines a location-awareness area of the healthcare establishment. Thus, if the module 100 is located within the location-awareness area, then the tag ID 106 encoded in the wireless beacon 110 emitted by the emitter 112 will be detectable by a subset of the detectors 54. Knowledge of the locations of the detectors in the subset gives an approximate idea as to where the module 100 is located within the location-awareness area; however, it is insufficient to pinpoint of the location of the module 100. Thus, the location calculation engine 58 is used for providing an estimate of the location of the module 100 (and other portable memory modules) that is sufficiently precise to enable the provision of location-dependent services.

One possible way to achieve a sufficiently precise estimate of location is on the basis of suitably precise time measurements obtained from the subset of the detectors 54, i.e., those detectors that have detected the wireless beacon 110. Another possible way to achieve a sufficiently precise estimate of location is on the basis of direction of arrival measurements obtained from the subset of the detectors 54. These and other techniques will be known to those skilled in the art, and some are described in U.S. patent application Ser. No. 11/065,047 to Graves et al., hereby incorporated by reference herein.

In summary, some of the detectors 54 will receive the wireless beacon 110 from the emitter 112. These detectors will detect the tag ID 106 encoded therein and communicate the tag ID 106, together with information (pertaining to, for example, time or direction of arrival) to the location computation engine 58 over the communication links 56. Based on this information and on knowledge of the locations of the detectors 54 within the location-awareness area of the healthcare establishment (as stored in the detector location database 62), the location computation engine 58 then determines the location of the module 110 within the healthcare establishment. The tag ID 106 and the location of the module 110 having just been determined are then stored in a tag location database 78. The tag location database 78 may also add a link from the tag ID 106 to the secondary tag ID 106A known to be pre-associated with the tag ID 106. The tag location database 78 is accessible to the network processing entity 18.

Figure 3:
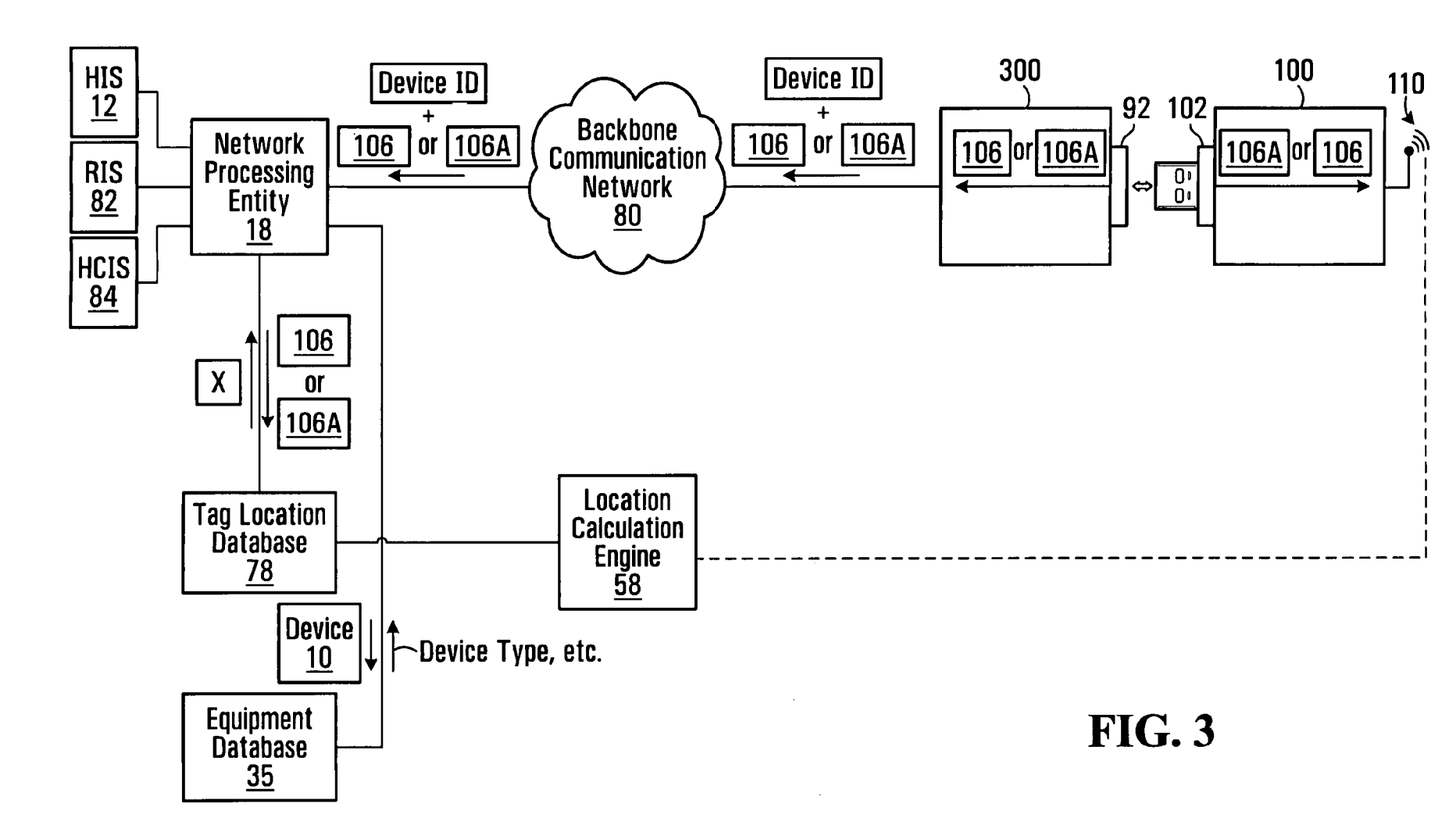
FIG. 3 shows formation of a connection-based association indicative of close physical proximity between the portable memory module of FIG. 2 and one of the electronic devices of FIG. 1A, in accordance with a non-limiting embodiment of the present invention.

The location calculation engine 58 continues to track, over time, the location of the module 100 in the above described manner while the module 100 itself may travel throughout the healthcare establishment. For example, the module 100 may be transported by a clinician or other user. At a given point in time, a connection-based association indicative of close physical proximity may be formed between the module 100 and one of the wired terminals 14A, one of the wireless terminals 14B or one of the medical devices 60. With reference now to FIG. 3, consider the case where, indeed, a connection-based association indicative of close physical proximity association is formed between the module 100 and one of the wired terminals 14A, one of the wireless terminals 14B or one of the medical devices 60, hereinafter referred to as an "electronic device 300".

In an example embodiment, where the module 100 and the electronic device 300 are equipped, respectively, with complementary interfaces 102, 92, the aforesaid connection-based association indicative of close physical proximity between the module 100 and the electronic device 300 can be formed by connecting the interface 102 of the module 100 to the interface 92 of the electronic device 300, such as by plugging in. In accordance with non-limiting embodiments of the present invention, the nature of the connection of the interface 102 of the module 100 to the interface 92 of the electronic device 300 is such that it allows (i) the module 100 to be rigidly supported by the electronic device 300 while the clinician uses the electronic device 300 and (ii) the location of the electronic device 300 to be established based on the location of the module 100, to within a sufficiently high degree of precision. In a non-limiting embodiment, the "sufficiently high degree of precision" may correspond to a threshold of several inches. For example, it may be desirable for the separation between the emitter 112 and an extremity of the electronic device not to exceed about 2-3 inches. Both of the above requirements are satisfied by providing the module 100 with a form factor and interface design similar to that of a standard USB memory stick, although this is not to be considered a limitation of the present invention and other possibilities will occur to those of skill in the art.

Following the formation of the above-mentioned connection-based association indicative of close physical proximity, the electronic device 300 obtains the tag ID 106 (or the secondary tag ID 106A) from the module 100 via the interface. This can be achieved by accessing the memory 104 of the module 100 via the processing entity 116.

The electronic device 300 now has access to the tag ID 106 (or the secondary tag ID 106A). Since the electronic device 300 is connected to the network processing entity 18 over the backbone communications network 80, the electronic device 300 communicates the tag ID 106 (or the secondary tag ID 106A) and the device ID to the network processing entity 18 over the backbone communications network 80. The device ID may take on different forms, such as a MAC address, serial number and the like. When the backbone communications network 80 is an IP-based network, the electronic device 300 may communicate the tag ID 106 (or the secondary tag ID 106A) and its device ID using IP packets.

From the perspective of the network processing entity 18, it receives knowledge that the tag ID 106 (or the secondary tag ID 106A) is linked to a certain device ID which, in this case, is the device ID of the electronic device 300. The network processing entity 18 then queries the tag location database 78 on the basis of the tag ID 106 (or the secondary tag ID 106A) received from the electronic device 300. Since the TDS 16 operates throughout this time, the database responds 78 by providing a data element "X" which is the current location of the module having the tag ID 106 (or secondary tag ID 106A). Since the module having the tag ID 106 (or secondary tag ID 106A) is in this case associated with the electronic device 300, the network processing entity 18 has thus established that "X" is the location of the electronic device 300.

Thus, it is possible to bring the equipment 60 or terminals 14A, 14B into an environment- and context-aware system (ECAS) at-will via the network processing entity 18 once the basic TDS 16 grid is deployed throughout the healthcare establishment, but without having to add location tracking and identification capability to the equipment 60 or terminals 14A, 14B.

The above description focused on the connection-based association indicative of close physical proximity formed between the module 100 and the electronic device 300, which is connected to the network processing entity 18 over the backbone communications network 80. Consider now the case of a connection-based association indicative of close physical proximity formed between the module 100 and a specific one of the non-networked devices 61. Here, the flow of information is in the reverse, namely the specific non-networked device provides the device ID to the module 100, where it is stored in the memory 104 together with a time stamp. At a later time, when a connection-based association indicative of close physical proximity is formed between the module and a device that is networked (e.g., the electronic device 300 referred to above), the previously collected device ID of the specific non-networked device and the time stamp are released to the electronic device 300, which forwards this information to the network processing entity 18 together with the device ID of the electronic device 300 and the tag ID 106 (or the secondary tag ID 106A) of the module 100 as described above. The network processing entity 18 can therefore not only establish that the electronic device 300 is at the current location of the module 100, but can also correlate the received time stamp with a location history for the module 100 (e.g., by tracking changes to the tag location database 78 for the tag ID 106) to identify a particular location, and then concluding that the specific non-networked device was at the particular location as the time indicated by the time stamp.

Further information regarding characteristics of the electronic device 300 (e.g., device type, device sub-type, display capability, etc.) can be obtained by consulting the equipment database 35 on the basis of the device ID. This allows the network processing entity 18 to provide services that are dependent on the location of the electronic device 300, without necessarily requiring knowledge of the location of the user of the electronic device 300. These services may involve retrieval of information from the HIS 12, RIS 82 or HCIS 84, processing of the retrieved information and transmittal of processed and/or retrieved information back to the electronic device 300. These services are increasingly useful as more and more medical equipment is driven by generic computer platforms. In particular, the network processing entity 18 can provide services that allow:

identification of suspicious motion of the electronic device 300;

control of radio frequency interference caused to nearby medical equipment;

prevention of transmittal of data outside a certain zone.

varying the display characteristics, display hysteresis and/or usability features of the electronic device 300. For instance, a medical device 60 used in a public area of the hospital may have different display characteristics, display hysteresis or usability features to when that device 60 is in a bed ward (intermediate public accessibility), an examination room (low public accessibility) or an operating room (no public accessibility). In addition, the nature of the material to be displayed may be modified as a function of location or the electronic device 300 may be disabled from functioning at all if left in a public place. Moreover, audio alerts could be adjusted to a lower level in a critical care wards versus a pediatric ward; or in and industrial manufacturing floor versus an office area;

inventory control, management and instrumentation fitness for use. A clinician can insert the module 100 which will then cause the electronic device 300 to be physically located and counted. The electronic device 300 can then be counted as in use by that clinician. The electronic device 300 can be validated as having current calibration from its (locally stored or centralized) calibration records to validate it is fit for use. The electronic device 300 can be tracked for security purposes. In addition, the electronic device 300 may be configured such that removal of the module 100 to cause an alarm, electronically and/or audibly, and to trigger appropriate security measures, cameras, etc. Thus, while the now untagged equipment's whereabouts are unknown, its last location is known and its maximum rate of movement can be estimated so security features (e.g., cameras, locks) can be activated at exits and choke-points within the building (such as stairwells, elevators, lobbies, etc.) to capture the identity of the perpetrators;

enabling of various emergency procedures. For example, code blue rapid team formation where critical equipment and clinicians are both required to save a person's life and may each be in a different location. The above techniques allow the equipment to be found, to be associated with specific clinicians who are part of the code blue team, and to be used to save a patient's life.

inventory tagging, such as tagging a piece of equipment requiring service for later pickup by technician;

monitoring. For example, the electronic device 300 can be instructed to monitor the environment rather than being a clinical tool. In particular, if the precise location of the electronic device 300 cannot be determined (e.g. due to location imprecision or theft), a picture could be taken and transmitted to the network processing entity 18 or stored.

robotic functions. For instance, certain devices, such as a medication delivery cart, may be self-driven and mobile yet also may benefit from association to the module 100 for security purposes. Knowing the location of the electronic device 300 can be beneficial even if the electronic device 300 has automated visual navigation aids, in case it should break down or theft (or attempted theft) occurs. The module 100 may be used as an identifier or control mechanism for manual or automated stocking and distribution of medication.

implementation of a maintenance routine. For example, certain medical equipment requires routine maintenance at regular intervals. A maintenance order an be triggered automatically, and the electronic device 300 can be instructed to enact a location beacon, and send an order to a technician.

Still other services will be apparent to those of ordinary skill in the art as being within the scope of the present invention.

In some instances, the network processing entity 18 may enhance the location-dependent services being provided to account for the location of the inferred or actual user of the electronic device 300. This can take the form of various scenarios, each of which assume by way of example but without limitation, that the user is a clinician. Three non-limiting scenarios are contemplated.

Figure 4A:
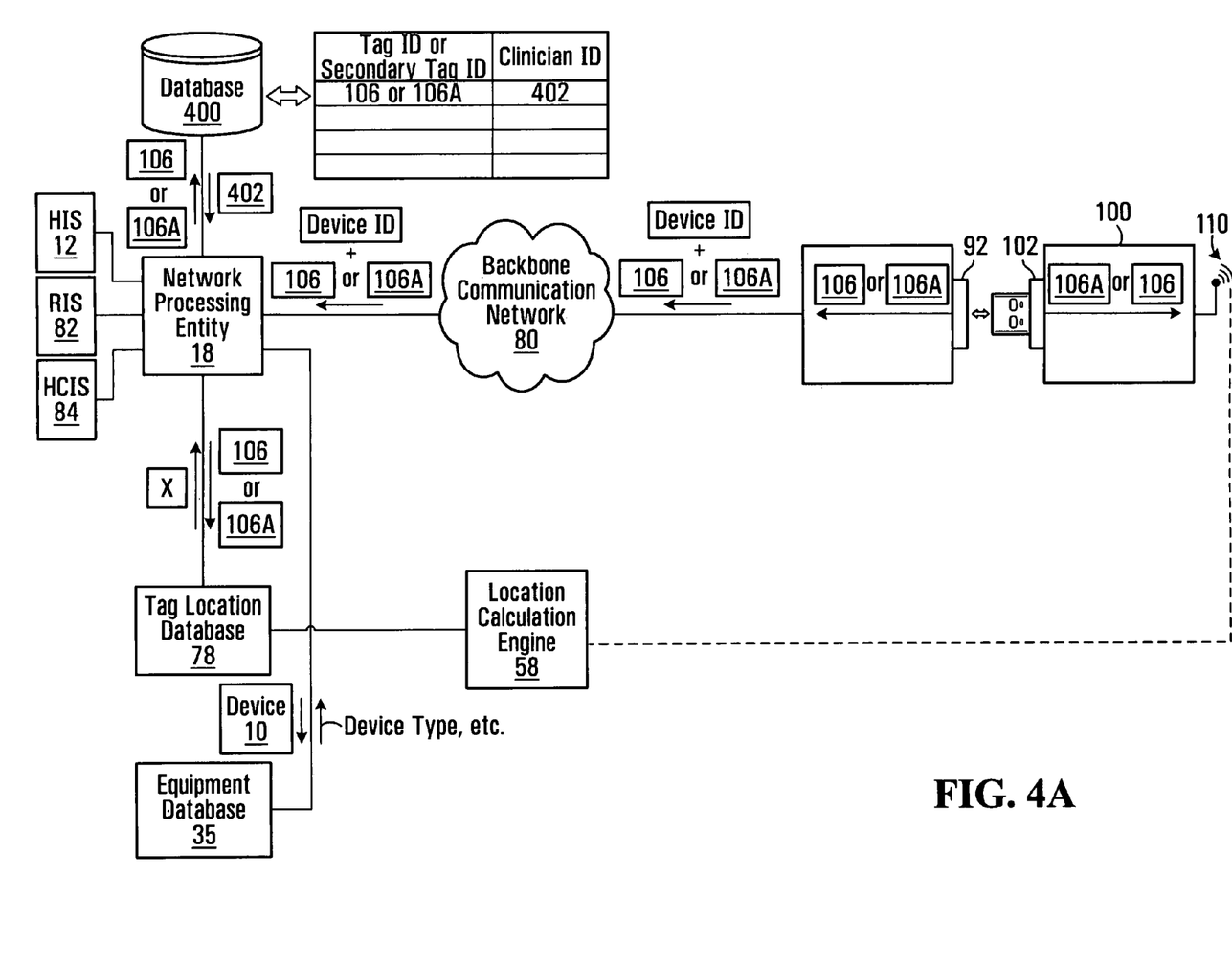
FIG. 4A shows formation of a connection-based association indicative of close physical proximity between the portable memory module of FIG. 2 and one of the electronic devices of FIG. 1A, in accordance with another non-limiting embodiment of the present invention wherein a clinician is pre-associated with the portable memory module.

In a first scenario, with reference to FIG. 4A, a database 400 is made accessible to the network processing entity 18. The database 400 stores the module's tag ID 106 (or the secondary tag ID 106A) together with a clinician ID 402 associated with a particular clinician. Thus, when the network processing entity 18 obtains knowledge of the tag ID 106 (or the secondary tag ID 106A), it can consult the database 400 to obtain the clinician ID 402 of the particular clinician. By virtue of this association between the particular clinician and the module 100, the network processing entity 18 infers that when a connection-based association indicative of close physical proximity is formed between the tag ID 106 (or secondary tag ID 106A) and the electronic device 300, the particular clinician is at the location of the electronic device 300 and is therefore likely to require interaction with the HIS 12, RIS 82 or HCIS 84. A further database in the HIS 12 or the HCIS 84 will allow the network processing entity 18 to obtain relevant information about the particular clinician based on the clinician ID 402. Such relevant information may include permissions, patient lists etc. This allows certain enhanced location-dependent services to be provided, such as:

customization of device functionality. For instance, consider the case where the electronic device 300 is a patient monitoring device 60 hooked up to a patient. In a generic mode of operation, the patient monitoring device 60 may present the necessary vital sign information for the patient. However, when the consulting physician arrives and inserts his pre-associated module 100, the patient monitoring device 60 may present a much more comprehensive set of information via a much richer (but likely more difficult to use) interface. Furthermore, the nature of the change in functionality may change with location or context, such as pre-operative information in the bed ward, pre-operative information in the anteroom of the OR, or post-operative information in the recovery room, in the case where the patient monitoring device 60 is portable and traveling with the patient.

use of a pool of unpersonalized devices. Consider a bank of tablet computers 14B sitting in a bank of tablet computer chargers, one of which can be taken from the chargers by a clinician and personalized to the clinician by plugging his or her respective module 100 into the tablet computer 14B. The memory 104 may contain patient data from the day's activity, which is added to by the new tablet computer 14B. When the battery runs low, the clinician returns the tablet computer 14B to the charger, which initiates a data transfer to the module 100 (if required) and allows the clinician to extract the module 100 having more patient data on it than before the tablet computer 14B was used, and the module 100 can now be used to personalize another tablet computer 14B with a fully charged battery.

the insertion of the module 100 into the electronic device 300 could also trigger various actions to be taken across a network, such as triggering the download of user preferences from a server, setting up a connection between that the electronic device 300 and another device which is also "keyed" to the same clinician, etc. Many other options are possible. The actions could be predefined or there may be a user interface enabling some form of user intervention (e.g., "Do you want to call user A or B?");

clinical process tracking and auditing. This could include medication dispensing and administering, or medical device adjustments. For example, consider the case where the electronic device 300 is an IV pump 60. The amount of medication being dispensed from the IV pump 60 can be adjusted based on the location of the pump 60 and the association of the clinician with the pump 60;

directions. Consider the case where a clinician is lost and plugs in to a terminal 14A in order to determine his/her current location and obtain directions. The directions may be associated with a computerized work order, for example to direct the clinician to a specific patient next on their list;

security. It should be appreciated that clinicians may be authorized to access certain terminal or device functions, or certain information, in one area and not another. For example they may be prohibited from viewing patient records in the lobby, or running a mobile ultrasound machine in a surgery ward.

Still other services will be apparent to those of ordinary skill in the art as being within the scope of the present invention.

Figure 4B:
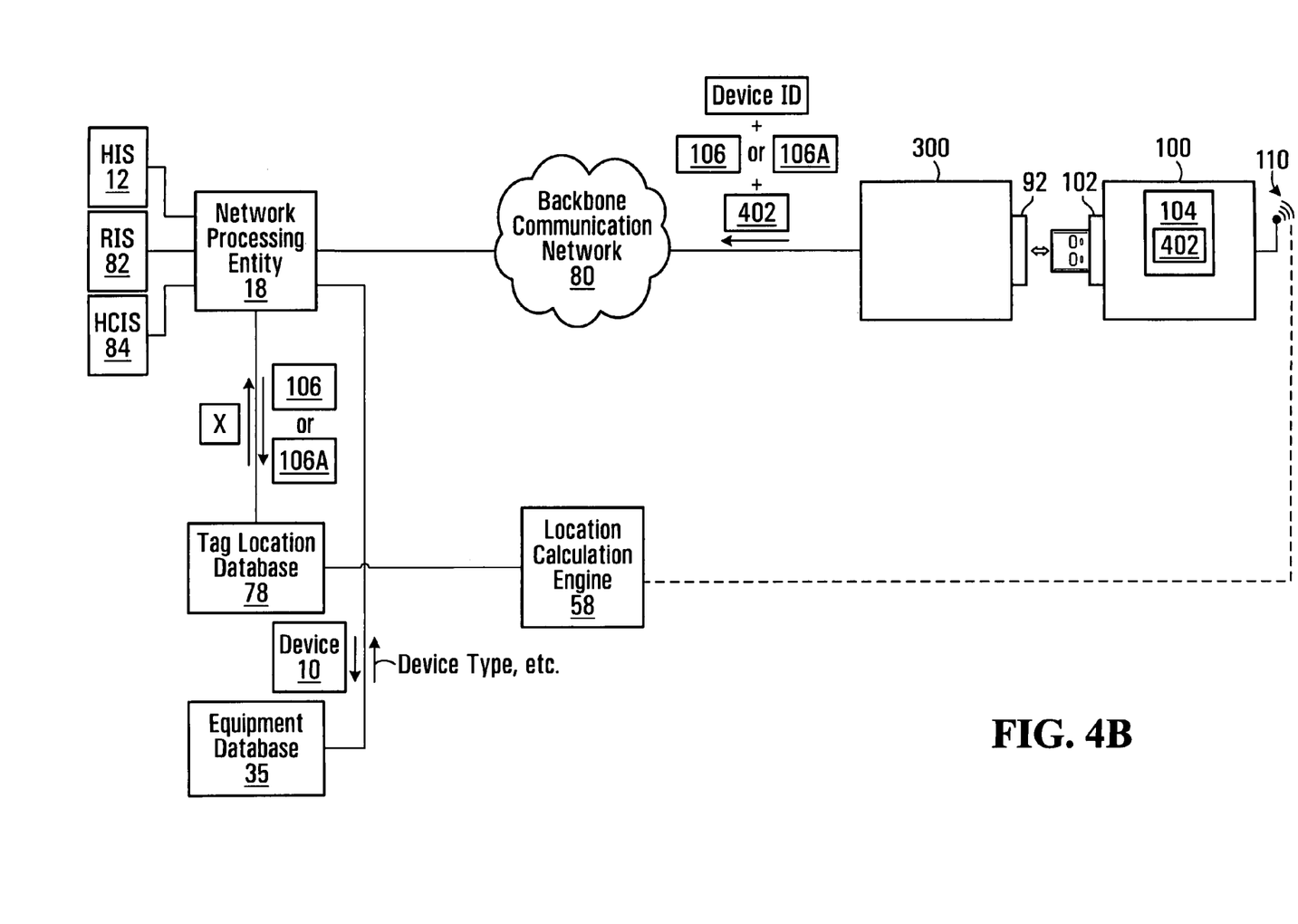
FIG. 4B shows formation of a connection-based association indicative of close physical proximity between the portable memory module of FIG. 2 and one of the electronic devices of FIG. 1A, in accordance with another non-limiting embodiment of the present invention wherein a clinician ID is stored in the portable memory module and provided to the electronic device.

In a second scenario, with reference to FIG. 4B, the memory 104 of the module 100 stores the clinician ID 402 in addition to the tag ID 106 and/or the secondary tag 106A. This eliminates the need for the database 400. Instead, in this scenario, when the connection-based association indicative of close physical proximity between the module 100 and the electronic device 300 is formed, the electronic device 300 obtains the clinician ID 402 and the tag ID 106 (or the secondary tag ID 106A) from the module 100. The electronic device 300 transmits the clinician ID 402 and the tag ID 106 (or the secondary tag ID 106A), together with its device ID, to the network processing entity 18. Once the location of the electronic device 300 is established based on the tag ID 106 (or the secondary tag ID 106A), the network processing entity 18 therefore also establishes that the particular clinician is at that location and is likely to require interaction with the HIS 12, RIS 82 or HCIS 84. Again, this allows enhanced location-dependent services to be provided as described above.

Figure 4C:
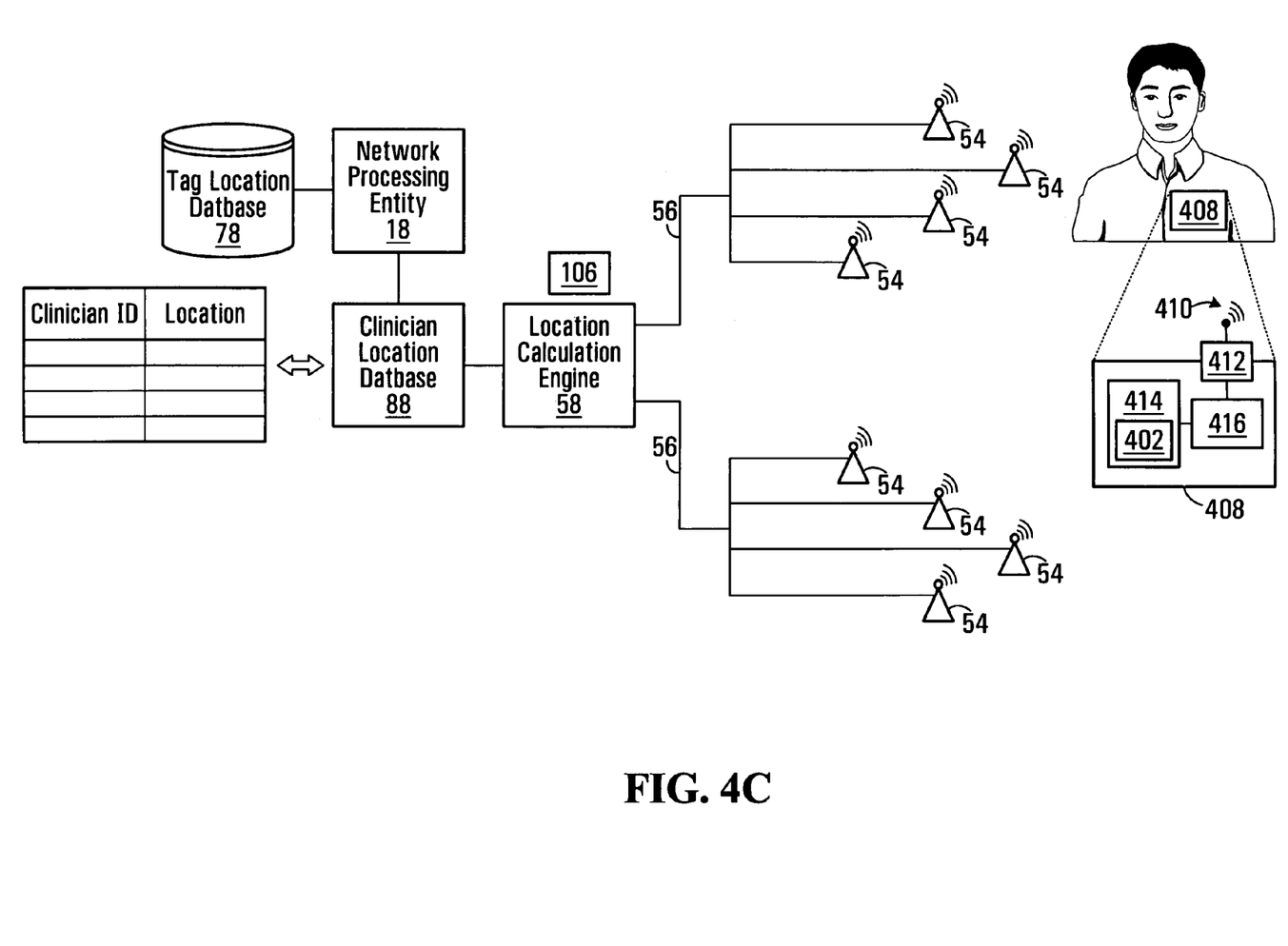
FIG. 4C illustrates detection of a clinician ID by the detection sub-system independently of detection of the portable memory module.

In a third scenario, with reference to FIG. 4C, the memory 104 of the module 100 does not store the clinician ID 402, nor is the clinician ID 402 pre-associated with the tag ID 106 (or the secondary tag ID 106A). Rather, a clinician tag 408 carried by the particular clinician includes a memory 414 and an emitter 412. The memory 414 stores the clinician ID 402. The clinician tag 408 includes a processing entity 416 with circuitry, control logic and/or software that is suitably configured to encode the clinician ID 402 into a signal that is transmitted via the emitter 412 as a wireless beacon 410. In a non-limiting embodiment, the wireless beacon 410 can be a brief radio frequency signal. In some non-limiting embodiments, the emitter 412 can be active (i.e., it emits the wireless beacon in an autonomous fashion), while in other non-limiting embodiments, the emitter 412 can be semi-active (i.e., it emits the wireless beacon a signal only in response to being interrogated), and in still other non-limiting embodiments, the emitter 412 can be passive (i.e., it reflects a received signal).

The detectors 54 detect the wireless beacon 412, and the location calculation engine 58 determines the location of the clinician tag 408. A clinician location database 88 stores the clinician ID 402 in association with the location determined by the location calculation engine 58. The clinician location database 18 is set up to be accessible to the network processing entity 18. In some embodiments, the clinician location database 88 could be combined with the tag location database 78.

With access to the clinician location database 88, the network processing entity 18 determines the location of the clinician tag that has the clinician ID 402, which is in this case clinician tag 408. In addition, as described above, access to the tag location database 78 allows the network processing entity 18 to determine the location of the electronic device 300. As a result, the network processing entity 18 can determine the proximity of particular clinician to the electronic device 300. This allows further enhanced location-dependent services to be provided, such as:

- if the clinician location is known relative to the electronic device 300 (into which the module 100 is plugged), then the screen of the electronic device 300 can be blocked when the clinician distances himself/herself from the device while the module 100 is still plugged in. This provides enhanced clinical privacy and security. Furthermore, the ongoing session can be blanked, suspended or terminated based upon the duration and distance of clinician/device separation characteristics from which a clinician intent can be inferred;
- if a clinician is authenticated to a particular terminal 14A using the module 100, then he/she can be reminded/contacted (e.g. via their pocket phone or pager) if they have wandered sufficiently far and for sufficiently long that they are deemed to be likely to have forgotten or lost the module 100;
- seamless services and single-sign-on. For example, the precise distance between the clinician and the module 100 enables single-sign-on and authentication. A clinician can more easily access the network and medical device functions, signing on with a password only once during the day;
- tailored information presentation. For example, if the location of the clinician is precisely determined, the information presented to him/her can be tailored in content and format. For example, if the clinician enters a patient's room and approaches a terminal 14A, the patient EHR and chart can be automatically pulled up when the module 100 is inserted into the terminal 14A, as well as notices or work orders that are relevant to the room.

Still other services will be apparent to those of ordinary skill in the art as being within the scope of the present invention.

Those skilled in the art will note that certain hospitals may be prohibited by law from offering to external physicians inducements to bring patients into the hospital—this includes providing the physicians with laptop and tablet computers. As a result, the physicians have to bring their own. The above approach allows such computers to be brought into the hospital and tracked within the hospital and made usable in the hospital when the module 100 is attached thereto, while reverting to being unusable in the hospital without the module 100.

Those skilled in the art will appreciate that in some embodiments, the functionality of the network processing entity 18 may be implemented using pre-programmed hardware or firmware elements (e.g., application specific integrated circuits (ASICs), electrically erasable programmable read-only memories (EEPROMs), etc.), or other related components. In other embodiments, the functionality of the network processing entity 18 may be achieved using a computing apparatus that has access to a code memory (not shown) which stores computer-readable program code for operation of the computing apparatus, in which case the computer-readable program code could be stored on a medium which is fixed, tangible and readable directly by the network processing entity 18, (e.g., removable diskette, CD-ROM, ROM, fixed disk, USB drive), or the computer-readable program code could be stored remotely but transmittable to the network processing entity 18 via a modem or other interface device (e.g., a communications adapter) connected to a network (including, without limitation, the Internet) over a transmission medium, which may be either a non-wireless medium (e.g., optical or analog communications lines) or a wireless medium (e.g., microwave, infrared or other transmission schemes) or a combination thereof.

Certain adaptations and modifications of the described embodiments can be made. Therefore, the above discussed embodiments are considered to be illustrative and not restrictive.

The invention claimed is:

1. A method, comprising:
   communicating with an electronic device to determine that a connection-based association indicative of close physical proximity has been formed between a portable module and the electronic device;
   determining a location of the portable module based on receipt of a wireless beacon emitted by the portable module;
   correlating the location of the portable module with the association between the portable module and the electronic device to establish that the electronic device has a location in close physical proximity to the location of the portable module; and
   causing the location of the portable module to be recorded in memory in association with the electronic device;
   wherein communicating with the electronic device comprises communicating over a backbone communications network.

2. The method defined in claim 1, wherein communicating over the backbone communications network comprises communicating over a connection that is at least partly wireless.

3. The method defined in claim 1, wherein communicating over the backbone communications network comprises communicating over a connection that is at least partly wired.

4. A method, comprising:
communicating with an electronic device to determine that a connection-based association indicative of close physical proximity has been formed between a portable module and the electronic device;
determining a location of the portable module based on receipt of a wireless beacon emitted by the portable module;
correlating the location of the portable module with the association between the portable module and the electronic device to establish that the electronic device has a location in close physical proximity to the location of the portable module; and
causing the location of the portable module to be recorded in memory in association with the electronic device;
wherein determining that the connection-based association indicative of close physical proximity has been formed comprises receiving from the electronic device an identifier of the portable module.

5. The method defined in claim 1, further comprising receiving the wireless beacon at a detection sub-system.

6. The method defined in claim 5, wherein determining the location of the portable module comprises processing information regarding at least one of an arrival time and a direction of arrival of the wireless beacon at each of a plurality of detectors in the detection sub-system.

7. The method defined in claim 4, wherein the wireless beacon includes the identifier of the portable module.

8. The method defined in claim 4, wherein the identifier of the portable module is a secondary identifier and wherein the wireless beacon includes an identifier of the portable module that is different from the secondary identifier.

9. The method defined in claim 4, further comprising receiving the wireless beacon at a detection sub-system.

10. The method defined in claim 9, wherein determining the location of the portable module comprises processing information regarding at least one of an arrival time and a direction of arrival of the wireless beacon at each of a plurality of detectors in the detection sub-system.

11. A method, comprising:
communicating with an electronic device to determine that a connection-based association indicative of close physical proximity has been formed between a portable module and the electronic device;
determining a location of the portable module based on receipt of a wireless beacon emitted by the portable module;
correlating the location of the portable module with the association between the portable module and the electronic device to establish that the electronic device has a location in close physical proximity to the location of the portable module;
causing the location of the portable module to be recorded in memory in association with the electronic device; and
delivering a service to the electronic device in a manner dependent on the location of the electronic device.

12. The method defined in claim 11, further comprising determining a clinician identifier, the clinician identifier identifying a clinician associated with the portable module.

13. The method defined in claim 12, further comprising delivering the service to the electronic device in a manner also dependent on the identity of the clinician associated with the portable module.

14. The method defined in claim 13, wherein determining the clinician identifier comprises receiving the clinician identifier from the electronic device.

15. The method defined in claim 13, further comprising receiving from the electronic device an identifier of the portable module to determine that the connection-based association indicative of close physical proximity has been formed, wherein determining the clinician identifier comprises querying a database with the identifier of the portable module in order to obtain the clinician identifier.

16. The method defined in claim 11, further comprising delivering the service to the electronic device in a manner dependent on a proximity of a clinician to the portable module.

17. The method defined in claim 16, further comprising determining the proximity of the clinician to the portable module.

18. The method defined in claim 17, wherein determining the proximity of the clinician to the portable module comprises determining a location of the clinician based on receipt of a second wireless beacon emitted by the clinician and evaluating the proximity of the clinician to the portable module by comparing the location of the portable module to the location of the clinician.

19. The method defined in claim 18, wherein the second wireless beacon includes an identifier of the clinician.

20. The method defined in claim 11, further comprising receiving the wireless beacon at a detection sub-system.

21. The method defined in claim 20, wherein determining the location of the portable module comprises processing information regarding at least one of an arrival time and a direction of arrival of the wireless beacon at each of a plurality of detectors in the detection sub-system.

22. A method, comprising:
communicating with an electronic device to determine that a connection-based association indicative of close physical proximity has been formed between a portable module and the electronic device;
determining a location of the portable module based on receipt of a wireless beacon emitted by the portable module;
correlating the location of the portable module with the association between the portable module and the electronic device to establish that the electronic device has a location in close physical proximity to the location of the portable module;
causing the location of the portable module to be recorded in memory in association with the electronic device;
receiving from the electronic device (i) a device identifier previously collected by the portable module from an other electronic device and (ii) data indicative of a past time at which the device identifier was collected;
consulting historical data regarding the portable module to establish a location of the portable module at said past time;
establishing that said other electronic device was located in close physical proximity to the location of the portable module at said past time; and
causing the location of the portable module at said past time to be recorded in memory in association with said other electronic device.

23. The method defined in claim 22, further comprising receiving the wireless beacon at a detection sub-system.

24. The method defined in claim 23, wherein determining the location of the portable module comprises processing information regarding at least one of an arrival time and a direction of arrival of the wireless beacon at each of a plurality of detectors in the detection sub-system.

25. A computer-readable storage medium comprising a set of instructions for execution by a computing device, wherein execution of the set of instructions by the computing device causes the computing device to execute a method that includes:
- communicating with an electronic device to determine that a connection-based association indicative of close physical proximity has been formed between a portable module and the electronic device;
- determining a location of the portable module based on receipt of a wireless beacon emitted by the portable module;
- correlating the location of the portable module with the association between the portable module and the electronic device to establish that the electronic device has a location in close physical proximity to the location of the portable module; and
- causing the location of the portable module to be recorded in memory in association with the electronic device,
- wherein communicating with the electronic device comprises communicating over a backbone communications network.

26. A computing device, comprising:
- communication circuitry, configured for communicating with at least an electronic device; and
- processing hardware coupled to the communication circuitry, wherein the processing hardware and the communication circuitry are configured to operate together to:
  - communicate with an electronic device to determine that a connection-based association indicative of close physical proximity has been formed between a portable module and the electronic device;
  - determine a location of the portable module based on receipt of a wireless beacon emitted by the portable module;
  - correlate the location of the portable module with the association between the portable module and the electronic device to establish that the electronic device has a location in close physical proximity to the location of the portable module; and
  - cause the location of the portable module to be recorded in memory in association with the electronic device;
- wherein determining that the connection-based association indicative of close physical proximity has been formed comprises receiving from the electronic device an identifier of the portable module.

27. A computer-readable storage medium comprising a set of instructions for execution by a computing device, wherein execution of the set of instructions by the computing device causes the computing device to execute a method that includes:
- communicating with an electronic device to determine that a connection-based association indicative of close physical proximity has been formed between a portable module and the electronic device;
- determining a location of the portable module based on receipt of a wireless beacon emitted by the portable module;
- correlating the location of the portable module with the association between the portable module and the electronic device to establish that the electronic device has a location in close physical proximity to the location of the portable module; and
- causing the location of the portable module to be recorded in memory in association with the electronic device;
- delivering a service to the electronic device in a manner dependent on the location of the electronic device.

28. A computer-readable storage medium comprising a set of instructions for execution by a computing device, wherein execution of the set of instructions by the computing device causes the computing device to execute a method that includes:
- communicating with an electronic device to determine that a connection-based association indicative of close physical proximity has been formed between a portable module and the electronic device;
- determining a location of the portable module based on receipt of a wireless beacon emitted by the portable module;
- correlating the location of the portable module with the association between the portable module and the electronic device to establish that the electronic device has a location in close physical proximity to the location of the portable module; and
- causing the location of the portable module to be recorded in memory in association with the electronic device;
- receiving from the electronic device (i) a device identifier previously collected by the portable module from an other electronic device and (ii) data indicative of a past time at which the device identifier was collected;
- consulting historical data regarding the portable module to establish a location of the portable module at said past time;
- establishing that said other electronic device was located in close physical proximity to the location of the portable module at said past time; and
- causing the location of the portable module at said past time to be recorded in memory in association with said other electronic device.

* * * * *